US011412955B2

(12) United States Patent
Ota et al.

(10) Patent No.: US 11,412,955 B2
(45) Date of Patent: Aug. 16, 2022

(54) BLOOD PRESSURE MEASURING APPARATUS AND BLOOD PRESSURE MEASURING METHOD

(71) Applicants: OMRON CORPORATION, Kyoto (JP); OMRON HEALTHCARE CO., LTD., Kyoto (JP)

(72) Inventors: Yuki Ota, Kyoto (JP); Tsuyoshi Kitagawa, Kyoto (JP); Shingo Yamashita, Kyoto (JP)

(73) Assignees: OMRON CORPORATION, Kyoto (JP); OMRON HEALTHCARE CO., LTD., Kyoto (JP)

( * ) Notice: Subject to any disclaimer, the term of this patent is extended or adjusted under 35 U.S.C. 154(b) by 224 days.

(21) Appl. No.: 16/554,869

(22) Filed: Aug. 29, 2019

(65) Prior Publication Data

US 2019/0380624 A1 Dec. 19, 2019

Related U.S. Application Data

(63) Continuation of application No. PCT/JP2018/009568, filed on Mar. 12, 2018.

(30) Foreign Application Priority Data

Mar. 15, 2017 (JP) .............................. JP2017-050224

(51) Int. Cl.
A61B 5/11 (2006.01)
A61B 5/021 (2006.01)
(52) U.S. Cl.
CPC ............ A61B 5/1116 (2013.01); A61B 5/021 (2013.01); A61B 2562/0219 (2013.01)
(58) Field of Classification Search
CPC .......... A61B 5/0205; A61B 2562/0219; A61B 5/4806–4818; A61B 2560/0209;
(Continued)

(56) References Cited

U.S. PATENT DOCUMENTS

2007/0239040 A1* 10/2007 Takeoka ................. A61B 5/021
600/485
2009/0216132 A1 8/2009 Orbach
(Continued)

FOREIGN PATENT DOCUMENTS

CN 101184434 5/2008
CN 101193588 6/2008
(Continued)

OTHER PUBLICATIONS

Instruction Manual, 2010, Omron Healthcare, Inc. (Year: 2010).*
(Continued)

Primary Examiner — David J. McCrosky
(74) Attorney, Agent, or Firm — Wenderoth, Lind & Ponack, L.L.P.

(57) ABSTRACT

A blood pressure measuring apparatus performs blood pressure measurement of a person to be measured. The apparatus includes: setting a measurement mode including at least a nocturnal blood pressure measurement mode to perform the measurement; and determining whether a blood pressure measurement posture is good under a first determination condition based on a height difference between a position of the apparatus and a heart position of the person in a sitting posture, and under a second determination condition based on a height difference between a position of the apparatus and a heart position of the person in a supine posture. A determination condition of the determining is switched to the second determination condition when the nocturnal blood pressure measurement mode is set.

13 Claims, 8 Drawing Sheets

(58) Field of Classification Search
CPC ......... A61B 5/002; A61B 5/021; A61B 5/022; A61B 5/1116; A61B 2560/0204; A61B 5/02141; A61B 5/1117
See application file for complete search history.

(56) References Cited

U.S. PATENT DOCUMENTS

| | | | |
|---|---|---|---|
| 2009/0216134 | A1 | 8/2009 | Hollinger et al. |
| 2013/0190629 | A1* | 7/2013 | Umeda .............. A61B 5/02225 600/479 |
| 2014/0207009 | A1 | 7/2014 | Sawanoi |

FOREIGN PATENT DOCUMENTS

| | | | |
|---|---|---|---|
| CN | 102119853 | | 7/2011 |
| CN | 103211587 | | 7/2013 |
| CN | 104665794 | | 6/2015 |
| CN | 204542117 | | 8/2015 |
| EP | 2 343 009 | | 7/2011 |
| JP | 5-176900 | | 7/1993 |
| JP | 2007-54648 | | 3/2007 |
| JP | 2007054648 A | * | 3/2007 |
| JP | 2009-247773 | | 10/2009 |
| JP | 2014-180361 | | 9/2014 |
| JP | 2014180361 A | * | 9/2014 |
| JP | 2014-233529 | | 12/2014 |
| JP | 2014233529 A | * | 12/2014 |
| JP | 2008538942 A | * | 11/2018 |
| WO | 2012/018029 | | 2/2012 |

OTHER PUBLICATIONS

International Preliminary Report on Patentability and Written Opinion of the International Searching Authority dated Sep. 17, 2019 in International (PCT) Application No. PCT/JP2018/009568.
International Search Report dated Apr. 24, 2018 in International (PCT) Application No. PCT/JP2018/009568 with English translation.
Office Action dated Apr. 28, 2020 in corresponding Japanese Patent Application No. 2019-506024 with English-language translation.
Office Action dated Aug. 26, 2021 in corresponding Chinese Patent Application No. 201880016428.1, with English-language translation.
Office Action dated Jan. 27, 2022 in Chinese Application No. 201880016428.1 with Machine translation.
Third Office Action dated Apr. 25, 2022 in Chinese Application No. 201880016428.1 with English translation.

* cited by examiner

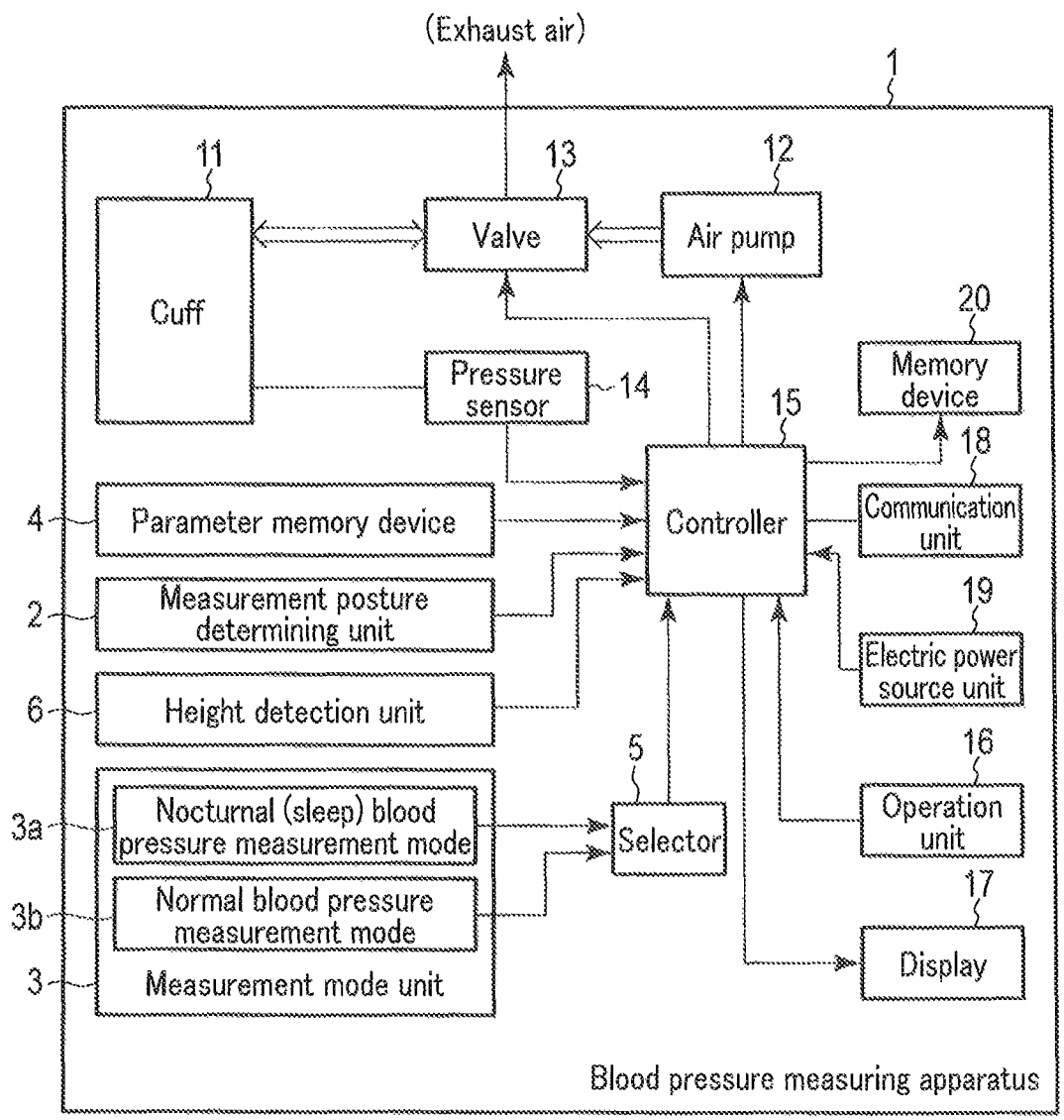
F I G. 1

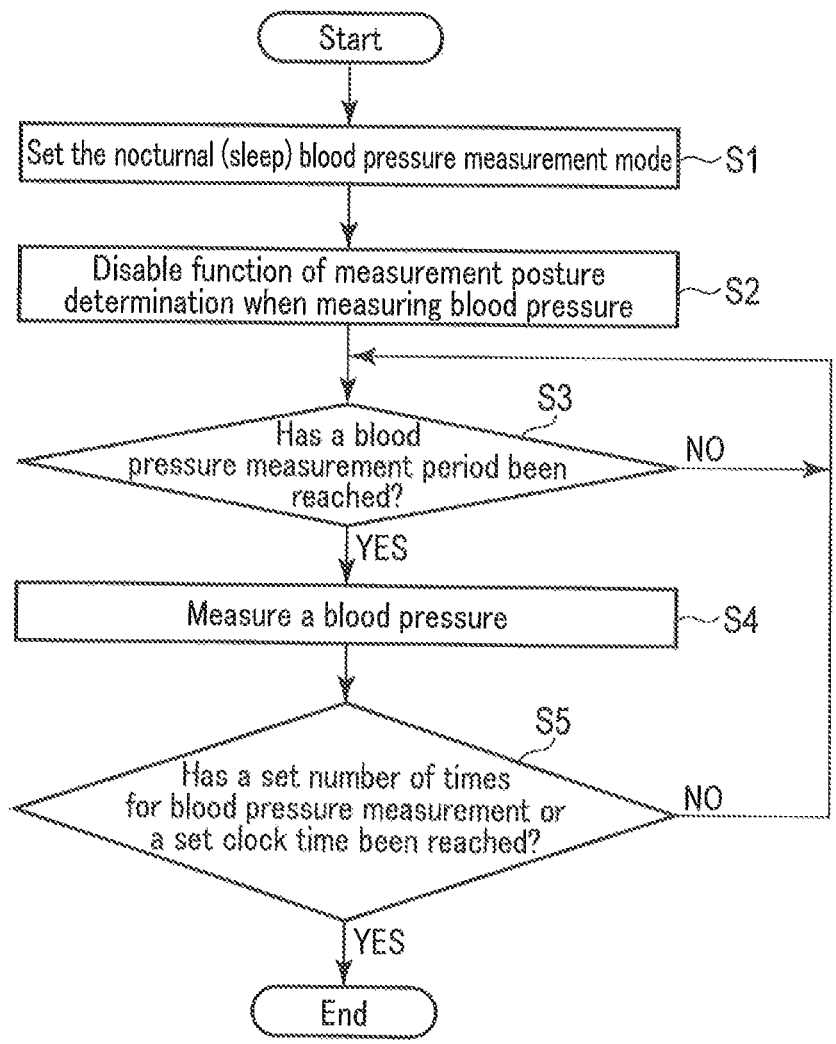
F I G. 2

BLOOD PRESSURE MEASURING APPARATUS AND BLOOD PRESSURE MEASURING METHOD

This application is a Continuation Application of PCT Application No. PCT/JP2018/009568, filed Mar. 12, 2018 and based upon and claiming the benefit of priority from Japanese Patent Application No. 2017-050224, filed Mar. 15, 2017, the entire contents of all of which are incorporated herein by reference.

FIELD

The present invention relates to a blood pressure measuring apparatus and a blood pressure measuring method for detecting a measurement posture of a person to be measured and performing blood pressure measurement according to the measurement posture.

BACKGROUND

It is generally said that a blood pressure measuring apparatus is positioned at the same height as the position of the person's heart to be measured when measuring a blood pressure to approximate the measured blood pressure value to a blood pressure value in the heart. For example, in Jpn. Pat. Appln. KOKAI Publication No. 2007-54648, it is confirmed that a blood pressure value is affected by gravity, and the measurement error is reduced by measuring the blood pressure value at a height close to the position of the heart. For this reason, in an upper arm type blood pressure measuring apparatus in which a cuff is wound around an upper arm, measurement is generally performed while a person to be measured is in a posture where an elbow of an arm is bent and placed on a desk.

Also, as a blood pressure measuring apparatus, a miniaturized wrist type blood pressure measuring apparatus to be worn on a wrist (forearm) is also used. Since this wrist type blood pressure measuring apparatus is positioned farther away from the position of the heart than the upper arm, it is recommended to perform the measurement while the wrist on which the apparatus is worn is placed on the chest to hold the apparatus close to the heart for high-measurement accuracy. The timing of blood pressure measurement is not limited to the morning and the evening. In recent years, along with increasing interest in disorders such as obstructive sleep apnea (OSP), blood pressure measurement during sleep has come to be performed.

In the blood pressure measurement described above, if the person to be measured is awake, measurement can be performed while the person to be measured is in the sitting posture on a chair or the like; on the other hand, if the person to be measured is sleeping, a posture of the person to be measured is supine or prone. The height difference between the position of the blood pressure measuring apparatus and the position of the heart in the sitting posture and the supine posture may be larger in a case of wearing a wrist type blood pressure measuring apparatus having a large movement range than in a case of wearing the upper arm type blood pressure measuring apparatus. In other words, the blood pressure value is more easily affected by the height when measured by the wrist type blood pressure measuring apparatus.

However, the sitting posture and the supine posture respectively have height differences caused between the position of the blood pressure measuring apparatus and the position of the heart. For this reason, whether or not the measurement position is correct cannot be appropriately determined by determining a measurement posture under the same determination condition in the sitting posture and the supine posture.

SUMMARY

A blood pressure measuring apparatus according to a first aspect of the present invention includes: a measurement mode unit having a measurement mode including at least a nocturnal blood pressure measurement mode to perform the blood pressure measurement intermittently; and a measurement posture determining unit that determines whether a blood pressure measurement posture is good or bad under a first determination condition based on a height difference between a position of the blood pressure measuring apparatus and a heart position of the person to be measured in a sitting posture of the person to be measured, and under a second determination condition based on a height difference between a position of the blood pressure measuring apparatus and a heart position of the person to be measured in a supine posture of the person to be measured, and switches a determination condition of the measurement posture determining unit to the second determination condition when the nocturnal blood pressure measurement mode is set by the measurement mode unit.

In the blood pressure measuring method according to the second aspect of the present invention, blood pressure measurement is performed with a determination function of the measurement posture determining unit being disabled when the nocturnal blood pressure measurement mode is set.

In the blood pressure measuring method according to the third aspect of the present invention, when the nocturnal blood pressure measurement mode is set and blood pressure measurement is performed, identification information is attached to a blood pressure value, for which a measurement posture at a time of the blood pressure measurement is determined to be bad by the measurement posture determining unit, and which is estimated to include a measurement error.

In the blood pressure measuring method according to the fourth aspect of the present invention, when the nocturnal blood pressure measurement mode is set, a parameter is changed to a second parameter for a supine posture, and a blood pressure value is obtained by blood pressure measurement based on the second parameter.

In the blood pressure measuring method according to the fifth aspect of the present invention, a correction value based on a height difference between a position of the blood pressure measuring apparatus and a heart position of the person to be measured is calculated in advance, blood pressure measurement is performed in the nocturnal blood pressure measurement mode, and a blood pressure value, for which a posture is determined to be bad by the measurement posture determining unit, is corrected with the correction value.

In the blood pressure measuring method according to the sixth aspect of the present invention, during blood pressure measurement in the nocturnal blood pressure measurement mode, a blood pressure value in a blood pressure measurement period in which a measurement posture is determined to be bad by the measurement posture determining unit is not acquired, and blood pressure measurement is performed again when a measurement posture is determined to be correct in a period other than the blood pressure measurement period and following the blood pressure measurement period.

According to the first embodiment of the present invention, in the sitting posture, supine posture, and blood pressure measurement, when the nocturnal (sleep) blood pressure measurement mode is set, measurement posture determination is performed in consideration of the height difference between the position of the blood pressure measuring apparatus and the heart position of the person to be measured in the supine posture, thereby obtaining a blood pressure value measured within an allowable range of the defined height difference at the time of measurement (measurement error of the measured blood pressure value).

According to the second embodiment of the present invention, when the nocturnal blood pressure measurement mode is set, the function of measurement posture determination is automatically disabled, and nocturnal blood pressure measurement is performed, thereby avoiding temporal suspension of the blood pressure measurement by the measurement posture determining unit and invalidation of the measured blood pressure value.

According to the third embodiment of the present invention, since the person to be measured who is asleep at night cannot adjust their posture by themselves, it is prioritized to continue the blood pressure measurement without interruption even if the measurement posture is bad. In the blood pressure measurement result, to the blood pressure value obtained at the time of an inferior posture, identification information indicating accordingly is attached; thus, it is possible to select only appropriate blood pressure values and use them for diagnosis.

According to the fourth embodiment of the present invention, by setting the nocturnal (sleep) blood pressure measurement mode, the second parameter for a supine posture is automatically selected and set. The correct blood pressure value can be obtained by blood pressure measurement based on the second parameter.

According to the fifth embodiment of the present invention, in the fourth blood pressure measuring method, a blood pressure value can be obtained by correcting the blood pressure value measured when the posture is determined to be bad by the measurement posture determining unit 2.

According to the sixth embodiment of the present invention, in blood pressure measurement in which the blood pressure measurement is performed again if it is determined that the measurement posture is bad and a problematic measurement error is included, unnecessary blood pressure measurement can be reduced by measuring the blood pressure when the posture is determined to be good.

BRIEF DESCRIPTION OF THE DRAWINGS

FIG. 1 is a block diagram showing a configuration example of a blood pressure measuring apparatus having a measurement posture determining unit according to one embodiment.

FIG. 2 is a flowchart for explaining a first blood pressure measuring method using the blood pressure measuring apparatus according to one embodiment.

DETAILED DESCRIPTION

Figure 3:
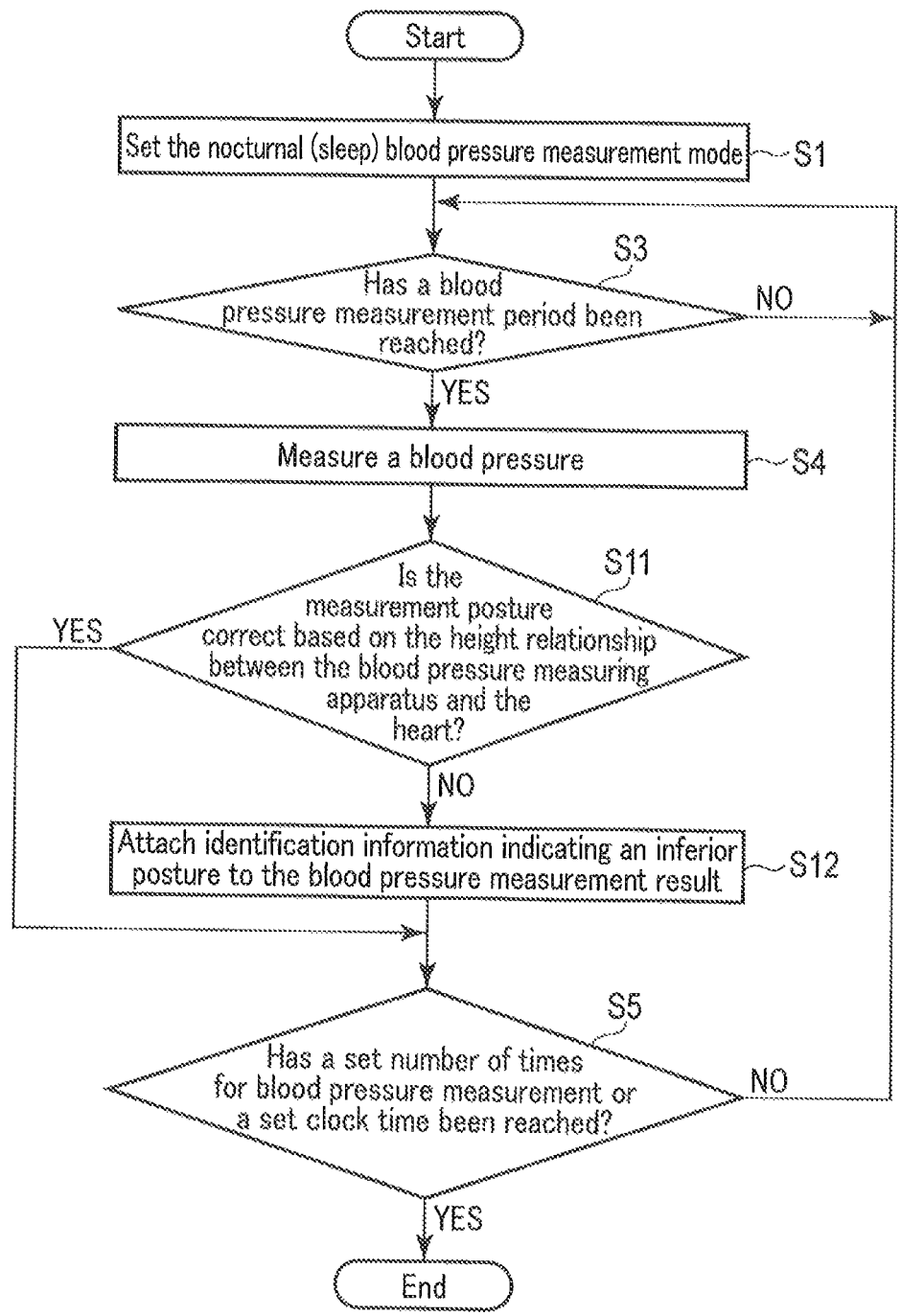
FIG. 3 is a flowchart for explaining a second blood pressure measuring method using the blood pressure measuring apparatus according to one embodiment.

Hereinafter, embodiments of the present invention will be described in detail with reference to the drawings.

An object of the present embodiments is to provide a blood pressure measuring apparatus which has a nocturnal (sleep) blood pressure measurement mode and performs a blood pressure measurement suitable for the measurement posture of the person to be measured at the time of blood pressure measurement, and a blood pressure measuring method.

First Embodiment

A blood pressure measuring apparatus according to one embodiment of the present invention will be described. FIG. 1 is a block diagram showing a configuration example of a blood pressure measuring apparatus having a measurement posture determining unit. In the present embodiment, a wrist type blood pressure measuring apparatus attached to the wrist, as an example of the attachment region, will be described. Of course, the region to which the apparatus is attached is not limited to the wrist, but may be the upper arm, and any integrated upper arm blood pressure measuring apparatus may be applied in the same manner.

This blood pressure measuring apparatus 1 includes, as main components for blood pressure measurement, a cuff 11 for applying pressure to the blood vessel at the part of the person co be measured to whom the apparatus is attached, an air pump 12 for supplying gas (air), a valve 13 for supplying air from the air pump 12 to the cuff 11 and exhausting air from the cuff 11 to the outside, a pressure sensor 14 for measuring the pressure inside the cuff and the blood pressure, and a controller 15 included in, for example, a computer for controlling the entire apparatus and performing blood pressure measurement. The person to be measured indicates a subject to be measured, for example a person to be measured.

The blood pressure measuring apparatus 1 further includes a display 17 that displays the detected blood pressure information, operation, etc., an operation unit 16 including operation buttons, a touch panel, etc. for measurement settings and various inputs, a communication unit 18 for communicating with an external device, an electric power source unit 19 including a rechargeable battery or a primary battery, and a memory device 20.

Among these components, the memory device 20 stores blood pressure values that are measured and associated with the time information by the controller 15 as needed. Further, the communication unit 18 is used mainly for transmitting the measured blood pressure information to an external device or the like. As a communication method, blood pressure information may be transmitted directly by wireless communication with an external device, or communication using a network such as a wireless LAN may be used.

As another communication method, for example, Bluetooth (registered trademark) may be used. Not only wireless communication but also optical communication and wired connection may be used. Although not shown in the drawings, a card recording device may be mounted to transmit blood pressure information by using a recording medium such as a small memory card.

Furthermore, the blood pressure measuring apparatus 1 is provided with a measurement mode unit 3 having a plurality of measurement modes such as a nocturnal (sleep) blood pressure measurement mode (or a nocturnal blood pressure measurement mode) 3a and a normal blood pressure measurement mode 3b, a selector 5, and a height detection unit 6. The present embodiment representatively presents two measurement modes, but various measurement modes may be constructed depending on the purpose of use. The selector 5 selects one of the above measurement modes in accordance with the operation of the operation unit 16 by the person to be measured or the measurer.

The normal blood pressure measurement mode is, for example, a measurement, mode used at the time of measurement in the daytime, the morning, and evening, and this mode includes manual measurement in which start or stop operation is performed and measurement is made continuously therebetween, and time setting measurement in which a measurement period is set. In the nocturnal (sleep) blood pressure measurement mode 3a, measurement is made a plurality of times with time intervals set discretionarily while the person to be measured is sleeping. This setting includes setting of the blood pressure measurement period and setting of the measurement timing. The measurement timing may be set based on the clock time such as 0 o'clock, 1 o'clock, . . . , or based on the number of times for measurement and the time interval between blood pressure measurement periods.

This nocturnal (sleep) blood pressure measurement mode can suppress the power consumption of the electric power source unit to a low level, and enables long time measurement. In the time setting, a clock function provided in the controller 15 is used.

The height detection unit 6 detects the position of the blood pressure measuring apparatus. Known techniques can be used for the height detection. For example, an acceleration signal generated by movement is measured by using a 3-axis acceleration sensor, and coordinate conversion is performed to obtain a vector, thereby detecting a height based on a change in the coordinate position. If the coordinate origin is set to the position of the heart, the height difference between the position of the blood pressure measuring apparatus 1 and the heart position of the person to be measured can be calculated. The setting to the coordinate origin can be made by resetting in a state where the blood pressure measuring apparatus 1 is placed at the position of the heart when activating the blood pressure measuring apparatus 1.

The measurement posture determining unit 2 determines whether the posture of the person to be measured detected by the height detection unit 6 is good or bad. In the present embodiment, since the posture for blood pressure measurement is determined, it is determined whether the person to be measured is in a sitting posture or a supine (or prone) posture, as roughly divided. Here, a height difference between the position of the blood pressure measuring apparatus 1 and the position of the heart of the person to be measured in the sitting posture of the person to be measured is a first determination condition. Further, a height difference between the position of the blood pressure measuring apparatus 1 and the heart position of the person to be measured in the supine posture of the person to be measured is a second determination condition. In addition, these differences in height expressed as blood pressure values are measurement errors generated at the time of a measurement. In the present embodiment, the supine posture and the prone posture are treated as being similar in terms of the height difference between the position of the blood pressure measuring apparatus and the position of the heart.

In the measurement posture in the present embodiment, the magnitude of the height difference between the position of the blood pressure measuring apparatus and the position of the heart affects the measured blood pressure value as a magnitude of a measurement error. A correct posture means that a height difference between the position of the blood pressure measuring apparatus and the position of the heart is small, and the measurement error between a blood pressure value measured by the blood pressure measuring apparatus and a blood pressure value which should be measured at the position of the heart is small, and the blood pressure value is within the allowable range as a value to be a basis for the doctor's examination. On the contrary, a bad posture means that, in the supine posture, the height difference is large, in other words, the measurement error is large, and the blood pressure value is out of the allowable range as a value to be a basis for the doctor's clinical examination. In short, the blood pressure value cannot be used even if the blood pressure value is measured.

In the case of the wrist, type blood pressure measuring apparatus, a height difference in the sitting posture is larger than a height difference in the supine posture. Therefore, there is a case where a blood pressure value measured in the sitting posture is determined to have a correct posture under the first determination condition, but may be determined to have a bad posture (an inferior posture) as compared with a blood pressure value which is measured when the person to be measured determined is in the supine posture and is determined under the second determination condition. Thus, the determination conditions (determination criteria) are different. In the blood pressure measuring method described below, if the nocturnal blood pressure measurement mode is set, the posture is a supine posture, and the posture is determined under the above-described second determination condition.

In the present embodiment, if the determination by the measurement posture determining unit 2 is used, the determination can be applied both before and after the blood pressure measurement. In other words, blood pressure measurement is not performed if the measurement posture determining unit 2 performs posture determination before blood pressure measurement and determines that the posture is bad. Also, if the posture is determined to be bad in the posture determination after blood pressure measurement, the corresponding blood pressure value at the memory device 20 is not stored. In addition, the measurement posture determining unit 2 reduces the power consumption of the electric power source unit 19 by starting the posture determination slightly before each blood pressure measurement period under control by the controller 15.

The parameter memory device 4 stores a parameter for a sitting posture and a parameter for a supine posture. The parameter for a supine posture is a parameter applied to the aforementioned second determination condition, and the parameter for a sitting posture is a parameter applied to the aforementioned first determination condition. Specifically, these parameters are thresholds based on which a blood pressure value is determined to be appropriate or measurement errors with which a blood pressure value is acceptable to be used for diagnosis, which are based on the aforementioned height difference between the position of the blood pressure measuring apparatus 1 and the heart position of the person to be measured.

As described above, in a sitting posture, a supine posture, and a blood pressure measurement, if the nocturnal (sleep) blood pressure measurement mode is set, the blood pressure measuring apparatus according to the present embodiment performs measurement posture determination in consideration of the height difference between the position of the blood pressure measuring apparatus and the heart position of the person to be measured in the supine posture, and can obtain a blood pressure value measured within an acceptable range of a defined height difference at the time of measurement (a measurement error of the measured blood pressure value).

Next, various blood pressure measuring methods using the blood pressure measuring apparatus having the above configuration will be described. A first blood pressure measuring method using the blood pressure measuring apparatus will be described with reference to the flowchart shown in FIG. 2.

The first blood pressure measuring method is a method of performing blood pressure measurement with the function of the measurement posture determining unit being automatically disabled when the nocturnal (sleep) blood pressure measurement mode is set. In the first blood pressure measuring method, the aforementioned first and second parameters are not used.

First, the measurer or the person to be measured activates the blood pressure measuring apparatus 1, and operates the operation unit 16 so as to select and set the nocturnal (sleep) blood pressure measurement mode from the measurement mode unit 3 by the selector 5 (step S1). Upon setting the nocturnal (sleep) blood pressure measurement mode, first, a blood pressure measurement period is specified, and a measurement start time (or a start clock time) and a measurement end time (or an end clock time) are set. Furthermore, time setting is made with given time intervals (for example, one hour), or time intervals between blood pressure measurement periods are set. In accordance with the setting of the nocturnal (sleep) blood pressure measurement mode, the controller 15 disables the function to detect and determine the measurement posture output from the measurement posture determining unit 2 (step S2). After that, blood pressure measurement is started from the measurement start time, and blood pressure measurement is performed (step S4) every time the blood pressure measurement period is reached (step S3).

Next, it is determined whether the set number of times for blood pressure measurement has been reached, or whether the set measurement end clock time has been reached (step S5). If it is determined in step S5 that the number of times for blood pressure measurement has not been reached or the measurement end clock time has not been reached (NO), the process returns to step S3 to continue the blood pressure measurement. On the other hand, if the number of times for blood pressure measurement has been reached or the measurement end clock time has been reached (YES), the blood pressure measurement ends. The blood pressure measurement value acquired by repeated measurement is stored in the memory device 20 in association with the time information by the controller 15 every time measurement is performed.

According to the first blood pressure measuring method, by disabling the determination function of the measurement posture determining unit, the posture determination is not affected even if the posture of the person to be measured is supine. Thus, blood pressure measurement can be performed without being affected by a supine posture in the nocturnal (sleep) blood pressure measurement mode.

Next, a second blood pressure measuring method using the blood pressure measuring apparatus will be described with reference to the flowchart shown in FIG. 3. In the second blood pressure measuring method, the same steps as those in the above first blood pressure measuring method are denoted by the same step numbers, and detailed descriptions thereof will be omitted.

The second blood pressure measuring method is a method where: the blood pressure measurement is continuously performed even if, when a blood pressure is measured in the nocturnal (sleep) blood pressure measurement mode, the measurement posture at the time of measurement is bad, namely, a measurement error is caused by the height difference between the position of the blood pressure measuring apparatus 1 and the position of the heart; and identification information is attached to a blood pressure value that is determined to indicate an inferior measurement posture and is estimated to include a measurement error.

First, the blood pressure measuring apparatus 1 is activated, and the nocturnal (sleep) blood pressure measurement mode is set (step S1). Then, blood pressure measurement is started from the measurement start time, and blood pressure measurement is performed (step S4) every time the blood pressure measurement period is reached (step S3).

The measurement posture determining unit 2 determines whether the measurement posture at the time of measurement of step S4 is good or bad (step S11). In this determination of whether the measurement posture is good or bad, if it is determined that the measurement posture is correct (YES), namely, there is no height difference between the position of the blood pressure measuring apparatus 1 and the position of the heart, or that the height difference is within the allowable range and the measurement error is not problematic, measurement time information is associated with the blood pressure value measured by the controller 15 and is stored in the memory device 20, and the process proceeds to the next step S5.

On the other hand, if the measurement posture is determined to be bad in the determination of step S11 (NO), namely, the height difference between the position of the blood pressure measuring apparatus 1 and the position of the heart is large, or the height difference exceeds the allowable range, and a problematic measurement error may be caused, the controller 15 attaches identification information indicating an inferior posture to the corresponding blood pressure value (step S12), and the blood pressure value is further associated with measurement time information and is stored in the memory device 20. Then, the process proceeds to the next step S5.

In the next step S5, it is determined whether the set number of times for blood pressure measurement has been reached, or whether the set measurement end clock time has been reached. If it is determined in step S5 that the number of times for blood pressure measurement has not been reached or the measurement end clock time has not been reached (NO), the process returns to step S3 to continue the blood pressure measurement. On the other hand, if the number of times for blood pressure measurement has been reached or the measurement end clock time has been reached (YES), the blood pressure measurement ends.

According to this second blood pressure measuring method, since the person to be measured sleeping at night cannot adjust their posture by themselves, it is prioritized to continue the blood pressure measurement without interruption even if the measurement posture is bad. In the blood pressure measurement result, to the blood pressure value obtained at the time of an inferior posture, identification information indicating accordingly is attached; thus, it is possible to select only appropriate blood pressure values and use them for diagnosis.

Figure 4:
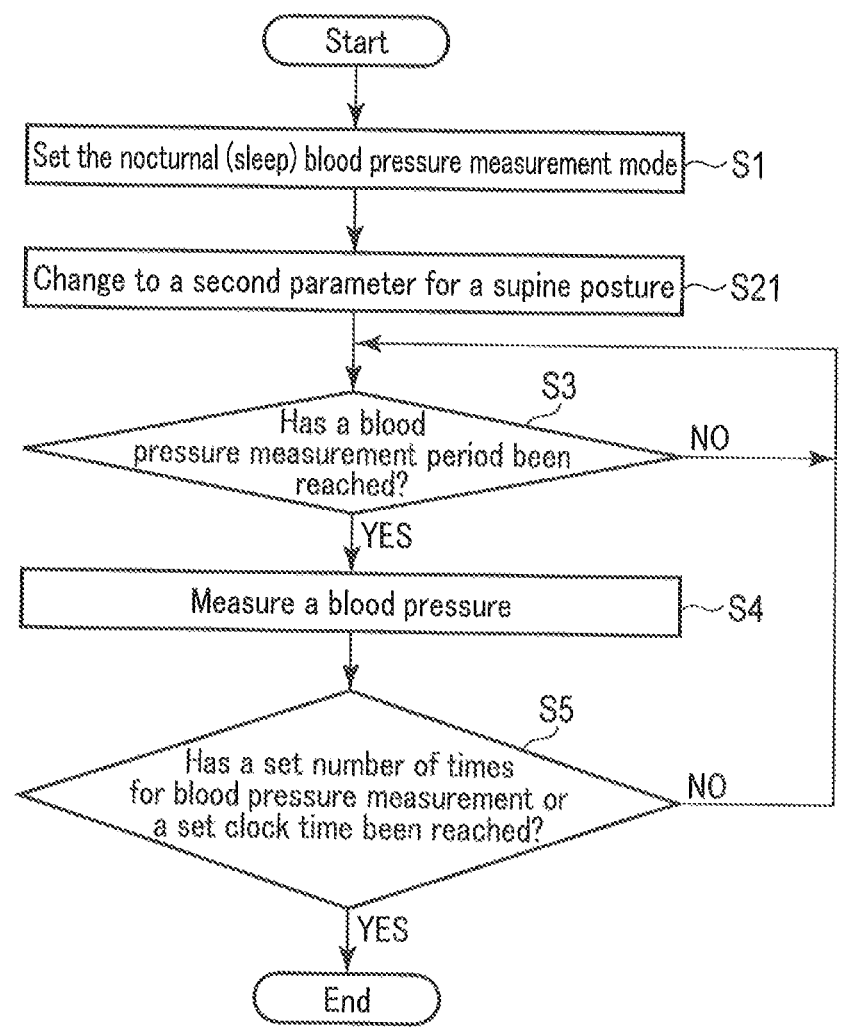
FIG. 4 is a flowchart for explaining a third blood pressure measuring method using the blood pressure measuring apparatus according to one embodiment.

Next, a third blood pressure measuring method using the blood pressure measuring apparatus will be described with reference to the flowchart shown in FIG. 4. In the third blood pressure measuring method, the same steps as those in the above first and second blood pressure measuring methods are denoted by the same step numbers, and the detailed description thereof will be omitted.

The third blood pressure measuring method is a method of automatically changing the setting to the second parameter for s supine posture when the nocturnal (sleep) blood pressure measurement mode is set, and using the second parameter for posture determination.

First, the blood pressure measuring apparatus 1 is activated, and the nocturnal (sleep) blood pressure measurement mode is set (step S1). With the setting of the nocturnal (sleep) blood pressure measurement mode, the controller 15 changes to the second parameter (step S21).

Then, blood pressure measurement is started from the measurement start time, and every time the blood pressure measurement period is reached (step S3), a blood pressure value is obtained by blood pressure measurement based on the second parameter (step S4). The measured blood pressure value is associated with measurement time information and stored in the memory device 20, and the process proceeds to the next step S5.

Next, it is determined whether the set number of times for blood pressure measurement has been reached, or whether the set measurement end clock time has been reached (step S5). If it is determined in step S5 that the number of times for blood pressure measurement has not been reached or the measurement end clock time has not been reached (NO), the process returns to step S3 to continue the blood pressure measurement. On the other hand, when the number of times for blood pressure measurement has been reached or the measurement end clock time has been reached (YES), the blood pressure measurement ends.

According to the third blood pressure measuring method, the second parameter for a supine posture is automatically selected and set by setting the nocturnal (sleep) blood pressure measurement mode. The correct blood pressure value can be obtained by blood pressure measurement based on the second parameter.

Figure 5:
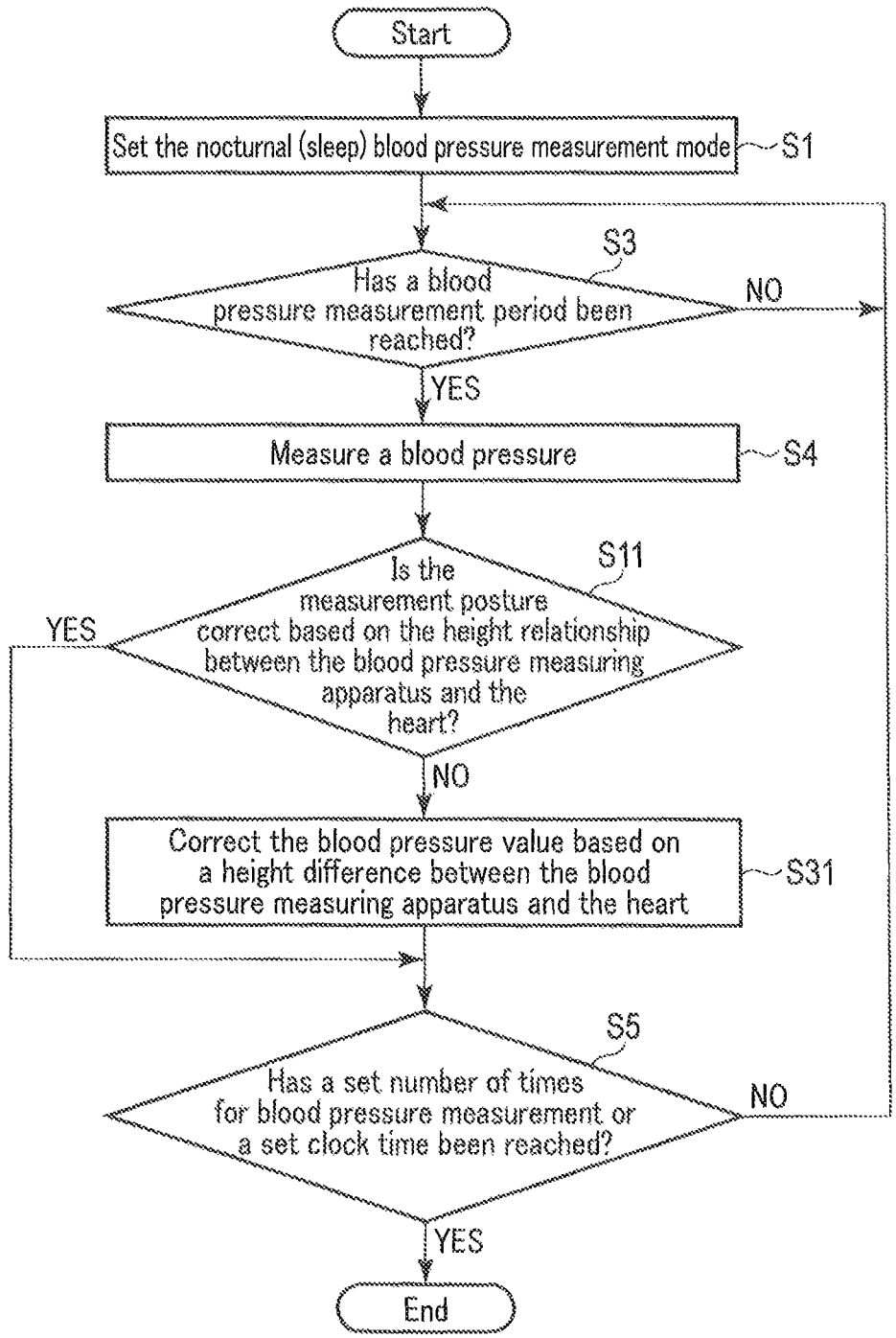
FIG. 5 is a flowchart for explaining a fourth blood pressure measuring method using the blood pressure measuring apparatus according to one embodiment.

Next, a fourth blood pressure measuring method using the blood pressure measuring apparatus will be described with reference to the flowchart shown in FIG. 5. In the fourth blood pressure measuring method, the same steps as those in the above first and second blood pressure measuring methods are denoted by the same step numbers, and the detailed description thereof will be omitted.

In the fourth blood pressure measuring method, a correction value based on the height difference between the position of the blood pressure measuring apparatus 1 and the position of the heart (it is recognized which of the positions of a blood pressure measuring apparatus and heart, is higher) is obtained in advance. This correction value can be obtained by a known calculation method using water head pressure. When a blood pressure is measured in the nocturnal (sleep) blood pressure measurement mode, if the measurement posture determining unit 2 determines that the posture is bad, the corresponding blood pressure value is corrected by the correction value based on the height difference. The height difference is preferably an actual measured value of the person to be measured person to be measured, but may be a value calculated from an average body type. The correction values are set for divided height differences, respectively.

First, the blood pressure measuring apparatus 1 is activated, and the nocturnal (sleep) blood pressure measurement mode is set (step S1). Then, blood pressure measurement is started from the measurement start time, and blood pressure measurement is performed (step S4) every time the blood pressure measurement period is reached (step S3). The measurement posture determining unit 2 determines whether the measurement posture at the time of measurement of step S4 is good or bad (step S11). In this determination of whether the measurement posture is good or bad, if it is determined that the measurement posture is correct (YES), namely, the measurement error is not problematic, the measured blood pressure value is associated with measurement time information without being corrected by the correction value in controller 15, and is stored in the memory device 20. Then, the process proceeds to the next step S5.

On the other hand, if the measurement posture is determined to be bad in the determination of step S11 (NO), namely, a problematic measurement error may be caused, the controller 15 corrects the corresponding blood pressure value by using the correction value (step S31). The corrected blood pressure value is associated with measurement time information by the controller 15 and is stored in the memory device 20, and the process proceeds to the next step S5.

In the next step S5, it is determined whether the set number of times for blood pressure measurement has been reached, or whether the set measurement end clock time has been reached. If it is determined in step S5 that the number of times for blood pressure measurement has not been reached or the measurement end clock time has not been reached (NO), the process returns to step S3 to continue the blood pressure measurement. On the other hand, if the number of times for blood pressure measurement has been reached or the measurement end clock time has been reached (YES), the blood pressure measurement ends.

According to the fourth blood pressure measuring method, a correct blood pressure value can be obtained by correcting the blood pressure value measured when the measurement posture determining unit 2 determines that the posture is bad.

Figure 6:
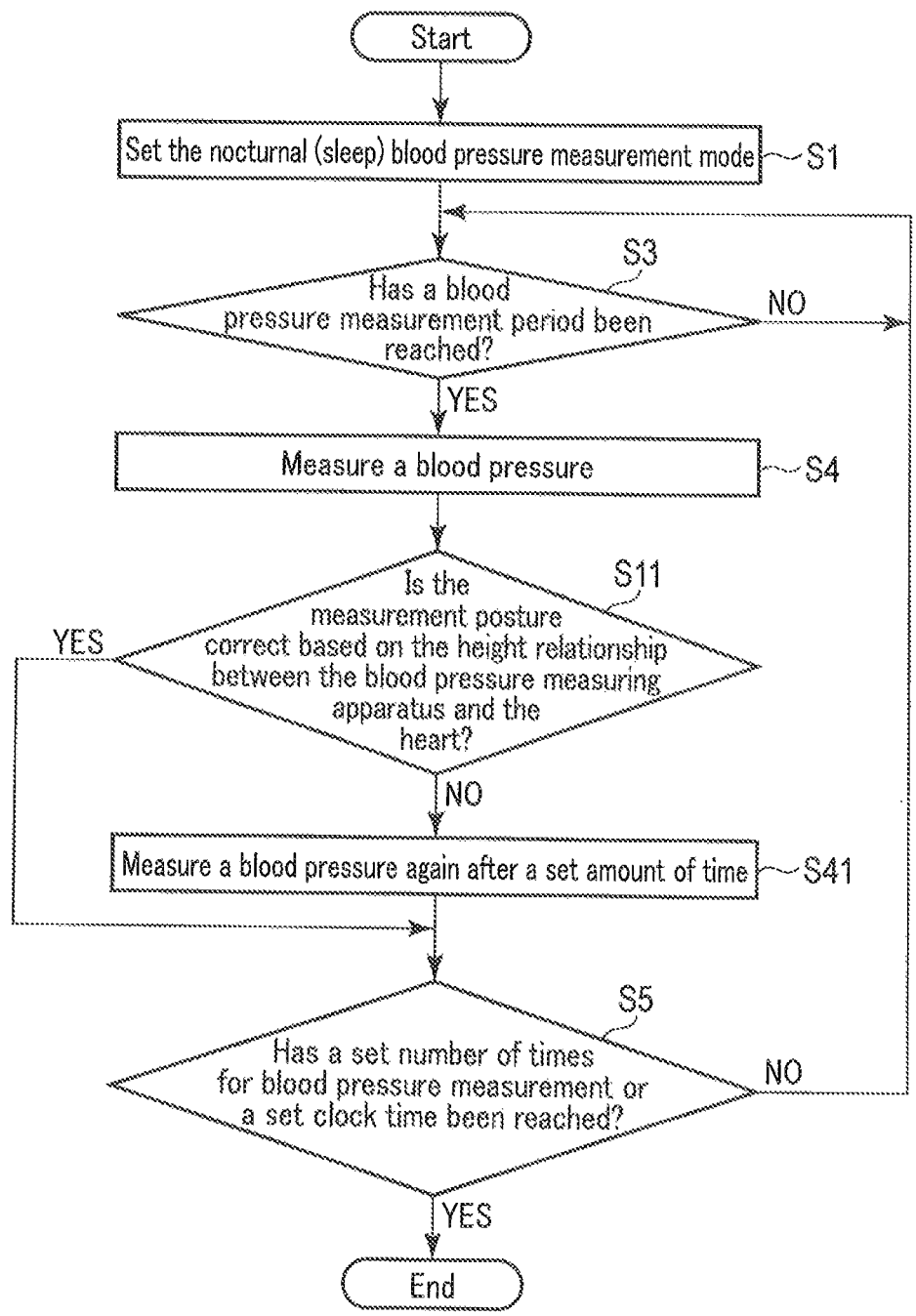
FIG. 6 is a flowchart for explaining a fifth blood pressure measuring method using the blood pressure measuring apparatus according to one embodiment.

Next, a fifth blood pressure measuring method using the blood pressure measuring apparatus will be described with reference to the flowchart shown in FIG. 6. In the fifth blood pressure measuring method, the same steps as those in the above first, and second blood pressure measuring methods are denoted by the same step numbers, and the detailed description thereof will be omitted.

This fifth blood pressure measuring method is a method where, if the measurement posture is determined to be bad when measuring a blood pressure in the nocturnal (sleep) blood pressure measurement mode for measuring a blood pressure intermittently, blood pressure measurement is performed again after a lapse of the set amount of time within a period which is following the blood pressure measurement period and other than the blood pressure measurement period.

First, the blood pressure measuring apparatus 1 is activated, and the nocturnal (sleep) blood pressure measurement mode is set (step S1). Then, blood pressure measurement is started from the measurement start time, and blood pressure measurement is performed (step S4) every time the blood pressure measurement period is reached (step S3). The measurement posture determination unit 2 determines whether the measurement posture at the time of measurement of step S4 is good or bad (step S11). In this determination of whether the measurement posture is good or bad, if it is determined that the measurement posture is correct (YES), namely, the measurement error is not problematic, the measured blood pressure value is associated with measurement time information without being corrected by the correction value in controller 15, and is stored in the memory device 20. Then, the process proceeds to the next step S5.

On the other hand, if the measurement posture is determined to be bad (NO) in the determination of step S11, namely, a problematic measurement error may be caused, the blood pressure is measured again after a lapse of the preset amount of time after the blood pressure measurement period and except for during the blood pressure measurement period (step S41), and the measured blood pressure value is associated with measurement time information and is stored in the memory device 20. Then, the process proceeds to the next step S5.

In the next step S5, it is determined whether the set number of times for blood pressure measurement has been reached, or whether the set measurement end clock time has been reached. If it is determined in step S5 that the number of times for blood pressure measurement has not been reached or the measurement end clock time has not been reached (NO), the process returns to step S3 to continue the blood pressure measurement. On the other hand, if the number of times for blood pressure measurement has been reached or the measurement end clock time has been reached (YES), the blood pressure measurement ends.

According to the fifth blood pressure measuring method, if it is determined that the measured blood pressure value may include a measurement error due to the height difference, it is possible to increase the number of data of the measured blood pressure value in the state where the measurement posture is correct by measuring a blood pressure again after a lapse of the preset amount of time from the blood pressure measurement period and except for during the blood pressure measurement period.

Figure 7:
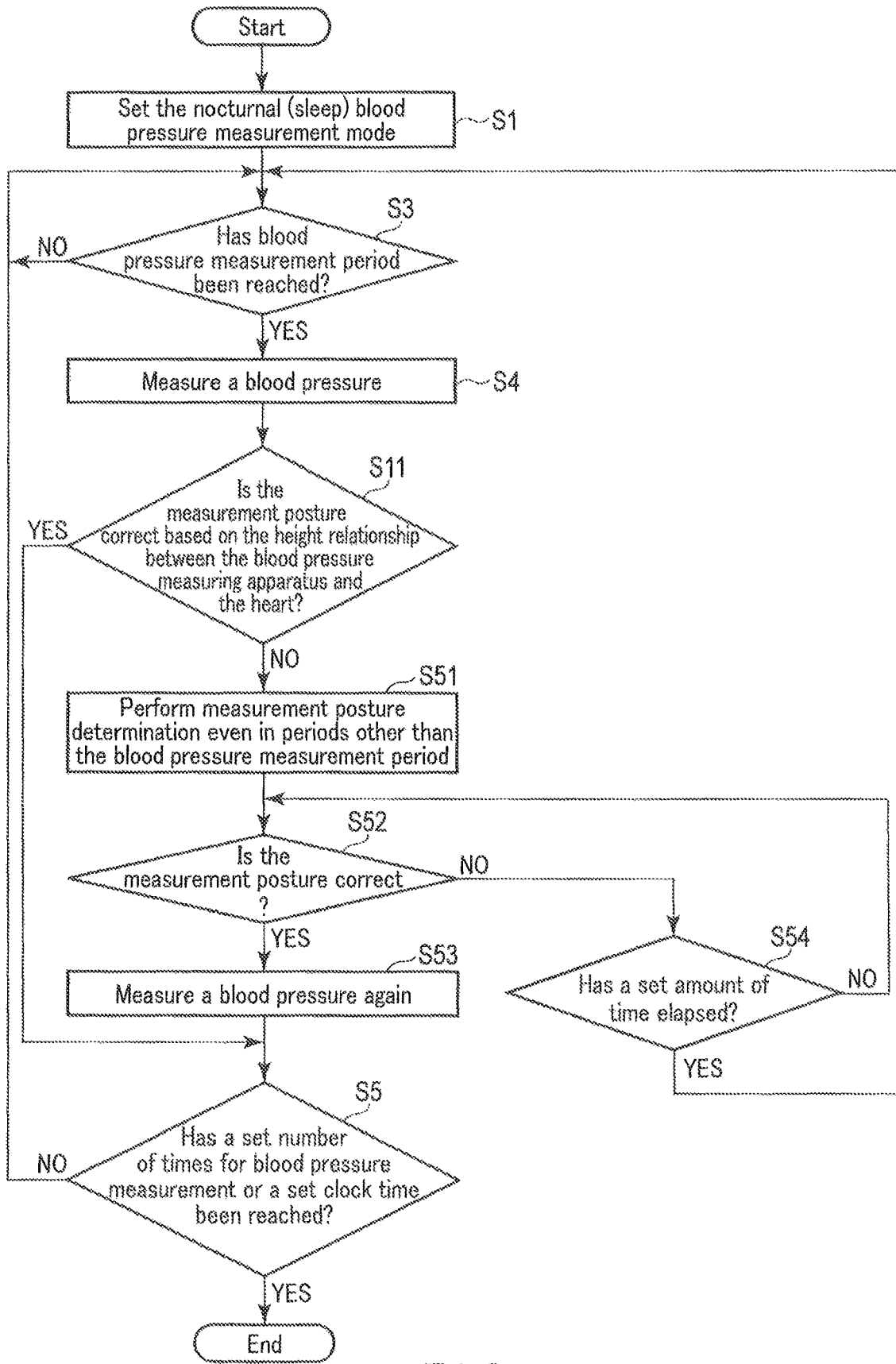
FIG. 7 is a flowchart for explaining a sixth blood pressure measuring method using the blood pressure measuring apparatus according to one embodiment.

Next, a sixth blood pressure measuring method using the blood pressure measuring apparatus will be described with reference to the flowchart shown in FIG. 7. In the sixth blood pressure measuring method, the same steps as those in the above first and second blood pressure measuring methods are denoted by the same step numbers, and the detailed description thereof will be omitted.

This sixth blood pressure measuring method is a method where, if the measurement posture is determined to be bad when measuring a blood pressure in the nocturnal (sleep) blood pressure measurement mode for measuring a blood pressure intermittently, blood pressure measurement is performed again when the measurement posture is determined to be good in a period other than the blood pressure measurement period.

First, the blood pressure measuring apparatus 1 is activated, and the nocturnal (sleep) blood pressure measurement mode is set (step S1). Then, blood pressure measurement is started from the measurement start time, and blood pressure measurement is performed (step S4) every time the blood pressure measurement period is reached (step S3). The measurement posture determining unit 2 determines whether the measurement posture at the time of measurement of step S4 is good or bad (step S11). In this determination of whether the measurement posture is good or bad, if it is determined that the measurement posture is correct (YES), namely, the measurement error is not problematic, the measured blood pressure value is associated with measurement time information without being corrected by the correction value in controller 15, and is stored in the memory device 20. Then, the process proceeds to the next step S5.

On the other hand, if the measurement posture is determined to be bad in the determination of step S11 (NO), namely, a problematic measurement error is caused, the controller 15 drives the measurement posture determining unit 2 to perform the measurement posture determination even in periods other than the blood pressure measurement period (step S51). If a correct measurement posture is obtained in this posture determination (step S52) or if a correct measurement posture is obtained in the determination of step S52 (YES), the blood pressure is measured again, and the measured blood pressure value is associated with measurement time information and is stored in the memory device 20. Then, the process proceeds to the next step S5. On the other hand, if a correct measurement attitude is not obtained in the determination of step S52 (NO), the measurement posture determination is continued, and it is determined whether the set amount of time has elapsed (step S54). If the set amount of time has elapsed (YES), the process returns to step S3.

In the next step S5, it is determined whether the set number of times for blood pressure measurement has been reached, or whether the set measurement end clock time has been reached. If it is determined in step S5 that the number of times for blood pressure measurement has not been reached or the measurement end clock time has not been reached (NO), the process returns to step S3 to continue the blood pressure measurement. On the other hand, if the number of times for blood pressure measurement has been reached or the measurement end clock time has been reached (YES), the blood pressure measurement ends.

According to the sixth blood pressure measuring method, unnecessary blood pressure measurement can be reduced by measuring a blood pressure if the posture is determined to be correct, in the blood pressure measurement to be performed again if it is determined that the measurement posture is bad and a problematic measurement error may be included.

Figure 8:
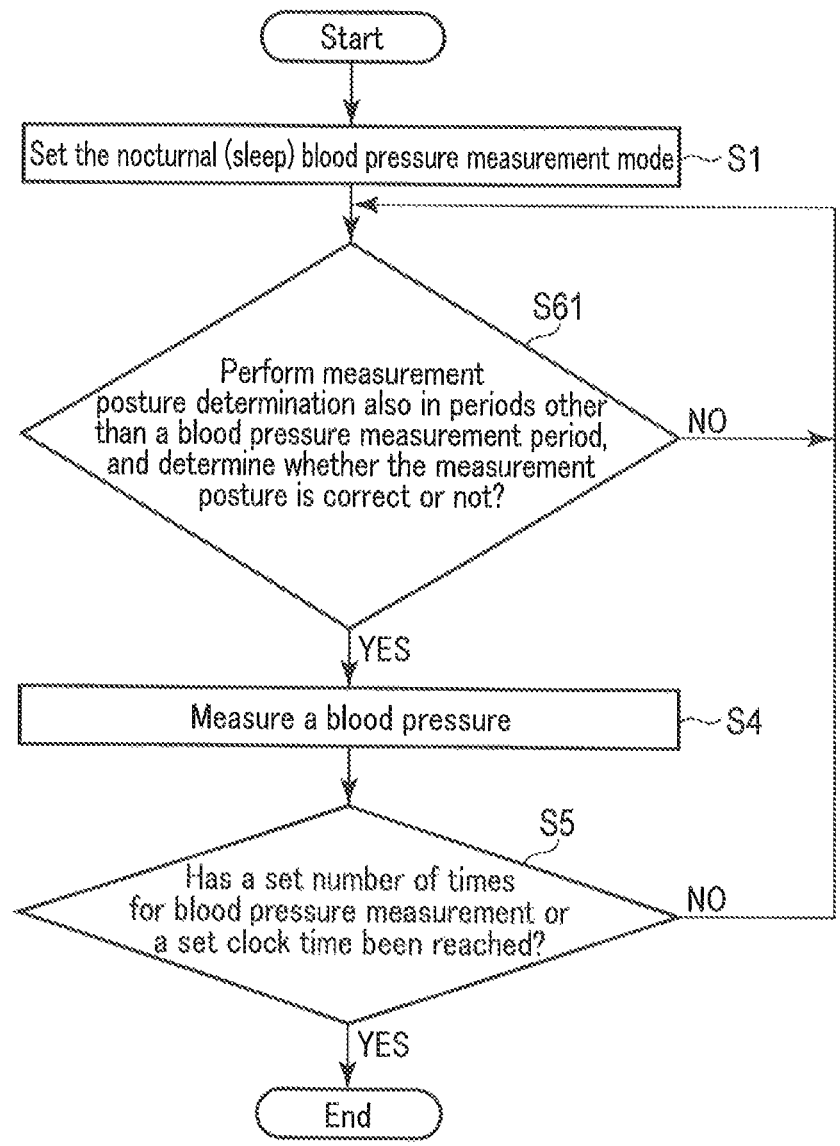
FIG. 8 is a flowchart for explaining a seventh blood pressure measuring method using the blood pressure measuring apparatus of one embodiment.

Next, a seventh blood pressure measuring method using the blood pressure measuring apparatus will be described with reference to the flowchart shown in FIG. 8. In the seventh blood pressure measuring method, the same steps as those in the above first and second blood pressure measuring methods are denoted by the same step numbers, and the detailed description thereof will be omitted.

This seventh blood pressure measuring method is a method of performing intermittent blood pressure measurement in the nocturnal (sleep) blood pressure measurement mode, performing measurement posture determination even in periods other than the blood pressure measurement period, and measuring a blood pressure when it is determined that the measurement posture is correct.

First, the blood pressure measuring apparatus 1 is activated, and the nocturnal (sleep) blood pressure measurement mode is set (step S1). At this time, the measurement posture determining unit 2 is constantly driven, and it is determined whether the measurement posture is good or bad also in periods other than the blood pressure measurement period (step S61). In this posture determination of step S61, the process waits until the measurement posture determining unit 2 obtains a measurement posture (NO), and if a correct measurement posture is obtained (YES), a blood pressure is measured (step S4), and the measured blood pressure value is associated with the measurement time information and is stored in the memory device 20. Then, the process proceeds to the next step S5.

In the next step S5, it is determined whether the set number of times for blood pressure measurement has been reached, or whether the set measurement end clock time has been reached. If it is determined in step S5 that the number of times for blood pressure measurement has not been reached or the measurement end clock time has not been reached (NO), the process returns to step S61 to continue the blood pressure measurement.

On the other hand, if the number of times for blood pressure measurement has been reached or the measurement end clock time has been reached (YES), the blood pressure measurement ends.

In the sixth blood pressure measuring method, assume that the measurement posture determining unit 2 continuously receives communication signals indicating a correct measurement posture in the blood pressure measurement of step S4. If the measured blood pressure information is stored in the memory device 20 each time of the signal reception, the data amount of the blood pressure information increases to greatly affect the memory capacity, and the measurement may end earlier than the scheduled clock time in the case where the end of measurement is set by the number of times for blood pressure measurement. Thus, the controller 15 sets the memory amount per unit time for blood pressure information input continuously, and if the information is in excess amount, invalidates the information without sending the information to the memory device 20 for reducing information amount by thinning, thereby optimizing the data amount of the blood pressure information stored in the memory device 20. When the thinning is performed, among the blood pressure values to be stored in the memory device 20, a blood pressure value having a feature (for example, a larger numerical value) compared to other adjacent blood pressure values on the data is preferentially stored.

According to the seventh blood pressure measuring method, a blood pressure is measured when an appropriate measurement posture is detected without setting a blood pressure measurement period, thereby excluding blood pressure information in which a problematic measurement error may be caused, and obtaining blood pressure information for only a correct measurement posture.

In the above embodiment, the cuff 11 is used for measuring a user's blood pressure value by, for example, an oscillometric method. However, the present invention is not limited thereto in the case of only measuring blood pressure values. For example, a pressure pulse wave sensor that detects a pressure pulse wave at each heartbeat may be provided to detect pressure pulse waves of the radial artery passing through the measured region (for example, the left wrist), so as to measure a blood pressure value (a systolic blood pressure value and a diastolic blood pressure value) (a tonometry method). The pressure pulse wave sensor may detect pulse waves of the radial artery passing through the measured region (for example, the left wrist) as a change in impedance, so as to measure a blood pressure value (an impedance method). The pressure pulse wave sensor may include a light-emitting element for radiating light toward an artery passing through a corresponding part of the measured region, and a light-receiving element for receiving reflected light (or transmitted light) of the radiated light, and detect pulse waves as a change in volume, so as to measure a blood pressure value (a photoelectric method). Moreover, the pressure pulse wave sensor may include a piezoelectric sensor in contact with the measured region, and detect a strain due to the pressure of an artery passing through a corresponding part of the measured region as a change in electric resistance, so as to measure a blood pressure value (piezoelectric method). Furthermore, the pressure pulse wave sensor may include a transmission element that transmits radio waves (transmission waves) toward an artery passing through a corresponding part of the measured region, and a reception element that receives reflection waves of the transmitted radio waves, and detect a change in distance between the artery and the sensor due to pulse waves of the artery as a phase shift between the transmission waves and the reflection waves, so as to measure a blood pressure value (a radio wave irradiation method). Any method can be employed other than the above methods as long as the method provides an observation of a physical quantity based on which a blood pressure value can be calculated.

The embodiment of the present invention described above includes the gist of invention as follows.

(1) A blood pressure measuring apparatus that is attached to a region of a person to be measured and performs blood pressure measurement, comprising:

a measurement mode unit having a measurement mode including at least a nocturnal blood pressure measurement mode to perform the blood pressure measurement intermittently;

a measurement posture determining unit that, when the nocturnal blood pressure measurement mode is set, detects a height difference between the position of the blood pressure measuring apparatus and the position of the heart of the person to be measured, and determines whether or not a posture is suitable for the blood pressure measurement based on whether or not a measurement error of a blood pressure value assumed from the height difference is within an allowable range; and a memory device configured to select and store a blood pressure value determined as a correct posture by the measurement posture determining unit.

The present invention is not limited to the invention described in the above embodiment, and may be changed variously in the range not deviating from its gist. Furthermore, various inventions for solving the above problems may be extracted by selecting or combining the plurality of disclosed structure elements.

The invention claimed is:

1. A blood pressure measuring apparatus that performs blood pressure measurement of a person to be measured, comprising a hardware controller including processing circuitry coupled to a memory, the hardware controller being configured to control the processing circuitry to:

set a measurement mode including at least a nocturnal blood pressure measurement mode to perform the blood pressure measurement intermittently while the person to be measured is sleeping; and determine whether a blood pressure measurement posture is a correct posture or a bad posture under a first determination condition based on a height difference between a position of the blood pressure measuring apparatus and a heart position of the person to be measured in a sitting posture of the person to be measured, and under a second determination condition based on a height difference between a position of the blood pressure measuring apparatus and a heart position of the person to be measured in a supine posture of the person to be measured, the correct posture being a measurement error of the blood pressure measuring apparatus within an allowable range, and the bad posture being a measurement error of the blood pressure measuring apparatus being out of the allowable range, and wherein a determination condition of the determining is switched to the second determination condition when the nocturnal blood pressure measurement mode is set by the setting the measurement mode.

2. A first blood pressure measuring method in the blood pressure measuring apparatus according to claim 1, comprising performing blood pressure measurement with a determination function of the measurement posture determining unit being disabled when the nocturnal blood pressure measurement mode is set.

3. A second blood pressure measuring method in the blood pressure measuring apparatus according to claim 1, comprising, when the nocturnal blood pressure measurement mode is set and blood pressure measurement is performed, attaching identification information to a measured blood pressure value, for the measured blood pressure value, a measurement posture at a time of the blood pressure measurement being determined to be bad by the measurement posture determining unit, and the measured blood pressure value being estimated to include a measurement error.

4. A third blood pressure measuring method in the blood pressure measuring apparatus according to claim 1, comprising, when the nocturnal blood pressure measurement mode is set, changing to a second parameter for the supine posture, and obtaining a blood pressure value by blood pressure measurement based on the second parameter.

5. A fourth blood pressure measuring method in the blood pressure measuring apparatus according to claim 1, comprising:

calculating a correction value based on a height difference between a position of the blood pressure measuring apparatus and a heart position of the person to be measured; and correcting, with the correction value, a blood pressure value for which a posture is determined to be bad by the measurement posture determining unit during blood pressure measurement in the nocturnal blood pressure measurement mode.

6. A fifth blood pressure measuring method in the blood pressure measuring apparatus according to claim 1, comprising, when performing blood pressure measurement in the nocturnal blood pressure measurement mode, not obtaining a blood pressure value in a blood pressure measurement period in which a measurement posture is determined to be bad by the measurement posture determining unit, and performing blood pressure measurement again when a measurement posture is determined to be correct in a period other than the blood pressure measurement period and following the blood pressure measurement period.

7. The apparatus according to claim 1, wherein the processing circuitry is further controlled to perform blood pressure measurement with a determination function of determining whether a blood pressure measurement posture is the correct posture or the bad posture being disabled when the nocturnal blood pressure measurement mode is set.

8. The apparatus according to claim 1, wherein the processing circuitry is further configured to, when the nocturnal blood pressure measurement mode is set and blood pressure measurement is performed, attach identification information to a measured blood pressure value, for the measured blood pressure value, a measurement posture at a time of the blood pressure measurement being determined to be bad by the measurement posture determining unit, and the measured blood pressure value being estimated to include a measurement error.

9. The apparatus according to claim 1, wherein the processing circuitry is further configured to, when the nocturnal blood pressure measurement mode is set, change to a second parameter for the supine posture, and obtain a blood pressure value by blood pressure measurement based on the second parameter.

10. The apparatus according to claim 1, wherein the processing circuitry is further configured to:

calculate a correction value based on a height difference between a position of the blood pressure measuring apparatus and a heart position of the person to be measured; and correct, with the correction value, a blood pressure value for which a posture is determined to be bad by the measurement posture determining unit during blood pressure measurement in the nocturnal blood pressure measurement mode.

11. The apparatus according to claim 1, wherein the processing circuitry is further configured to, when performing blood pressure measurement in the nocturnal blood pressure measurement mode, refrain from obtaining a blood pressure value in a blood pressure measurement period in which a measurement posture is determined to be bad by the determining whether the blood pressure measurement posture is good or bad, and perform blood pressure measurement again when a measurement posture is determined to be correct in a period other than the blood pressure measurement period and following the blood pressure measurement period.

12. A blood pressure measuring apparatus that performs blood pressure measurement of a person to be measured, comprising a hardware controller including processing circuitry coupled to a memory, the hardware controller being configured to control the processing circuitry to:

set at least a first mode and a second mode, the first mode being a normal blood pressure measurement mode to perform the blood pressure measurement manually manipulated, and the second mode being a nocturnal blood pressure measurement mode to perform the blood pressure measurement intermittently while the person to be measured is sleeping;

determine whether a blood pressure measurement posture is a correct posture or a bad posture under a first determination condition based on a height difference between a position of the blood pressure measuring apparatus and a heart position of the person to be measured in a sitting posture of the person to be measured;

determine whether the blood pressure measurement posture is the correct posture or the bad posture when the first mode is set; and perform blood pressure measurement with a determination function of determining whether the blood pressure measurement posture is the correct posture or the bad posture being disabled when the second mode is set, wherein the correct posture is a measurement error of the blood pressure measuring apparatus within an allowable range, and the bad posture is a measurement error of the blood pressure measuring apparatus being out of the allowable range.

13. A non-transitory computer readable medium storing a computer program which is executed by a computer for performing blood pressure measurement to provide the steps of:

setting a measurement mode including at least a nocturnal blood pressure measurement mode to perform the blood pressure measurement intermittently while the person to be measured is sleeping;

determining whether a blood pressure measurement posture is a correct posture or a bad posture under a first determination condition based on a height difference between a position of the blood pressure measuring apparatus and a heart position of the person to be measured in a sitting posture of the person to be measured, and under a second determination condition based on a height difference between a position of the blood pressure measuring apparatus and a heart position of the person to be measured in a supine posture of the person to be measured, the correct posture being a measurement error of the blood pressure measuring apparatus within an allowable range, and the bad posture being a measurement error of the blood pressure measuring apparatus being out of the allowable range; and performing blood pressure measurement with a determination function of determining whether a blood pressure measurement posture is the correct posture or the bad posture being disabled when the nocturnal blood pressure measurement mode is set, wherein a determination condition of the determining whether a blood pressure measurement posture is the correct posture or the bad posture is switched to the second determination condition when the nocturnal blood pressure measurement mode is set by the setting the measurement mode.

* * * * *